United States Patent [19]

Li

[11] 4,219,468

[45] * Aug. 26, 1980

[54] TRITIATED β-ENDORPHIN

[75] Inventor: Choh H. Li, Berkeley, Calif.

[73] Assignee: Hoffmann-La Roche Inc., Nutley, N.J.

[*] Notice: The portion of the term of this patent subsequent to Jun. 20, 1992, has been disclaimed.

[21] Appl. No.: 960,253

[22] Filed: Nov. 13, 1978

[51] Int. Cl.$^2$ ............................................. C07C 103/52
[52] U.S. Cl. ................................................ 260/112.5 R
[58] Field of Search ................................. 260/112.5 R

[56] References Cited

U.S. PATENT DOCUMENTS

| | | | |
|---|---|---|---|
| 4,038,222 | 7/1977 | Li | 260/112.5 R |
| 4,096,237 | 6/1977 | Li | 260/112.5 R |

OTHER PUBLICATIONS

Lemaire et al., J. Am. Chem. Soc., 99, 1577–1580, (1977).
J. Ramachandras et al., Biochimica et Biophysica Acta., 496, (1977), 321–328.

Primary Examiner—Delbert R. Phillips
Attorney, Agent, or Firm—Jon S. Saxe; Bernard S. Leon; George M. Gould

[57] ABSTRACT

Tritiated β-endorphin is prepared by catalytic tritiation of a [3,5-diido-Tyr]-β-endorphin which in turn is readily obtained by solid phase synthesis. The tritiated β-endorphin preferably [3,5-diiodo-Tyr$^{27}$]-β-endorphin may be utilized as a radio-labelled tracer compound in radioimmunoassay for β-endorphin and also exhibits biological activity comparable to that of the native β-endorphin.

4 Claims, No Drawings

TRITIATED β-ENDORPHIN

BACKGROUND OF THE INVENTION

An immunoassay for β-endorphin including the use of various radiolabelled β-endorphin tracer compounds is described in U.S. Pat. No. 4,096,237, issued June 20, 1978, inventor, C. H. Li. Tritiated β-endorphin is disclosed in such patent.

The synthesis of $N^\alpha$-Boc-3,5-diiodotyrosine-(OBrBzl) is described by Lemaire et al., J. Am. Chem. Soc. 99, 1577 (1977).

Tritiation of a 3,5-diiodotyrosine ACTH analog is disclosed by Ramachandran and Behrens, Biochem. Biophys. Acta 496, 321 (1977).

DESCRIPTION OF THE INVENTION

The present invention relates to the preparation of tritiated β-endorphin, particularly tritiated human β-endorphin, by catalytic tritiation of an iodinated tyrosine containing β-endorphin analog. Such tritiation is conveniently carried out using palladium oxide as catalyst in a manner known per se. Note Ramachandran and Behrens, supra.

Suitable iodinated tyrosine-β-endorphin analogs useful as substrates for tritiation herein include [3,5-$I_2$-Tyr$^1$]-, [3,5-$I_2$-Tyr$^{27}$]- and [3,5-$I_2$-Tyr$^{1,27}$]-β-endorphin.

EXAMPLE 1

[3,5-$I_2$-Tyr$^{27}$]-β-endorphin was utilized by the solid-phase method as described in Example 6 of U.S. Pat. No. 4,038,222 with the exception that $N^\alpha$Boc-O-BrBzl-3,5-$I_2$-Tyr is substituted for the corresponding tyrosine moiety in position 27 and chloromethylated styrene-divinylbenzene polymer is used. The iodinated peptide (6 mg, 1.5 μmole) was dissolved in 305 drops of 0.1 N HOAc, followed by 2.0 ml each of freshly distilled HMPA and DMA. To remove most of the water and HOAC from the reaction solution, it was evacuated at 21° C. to 0.05 mm Hg and kept at this pressure for approximately 45–60 min. This resulted in an approximate one-third reduction in volume and removed greater than 90% of the water as shown by NMR spectroscopy. The reaction solution could be kept frozen indefinitely at −70° before use. The catalyst used was PdO, finely ground to a dust in a glass mortar and pestle. An equal weight of catalyst to peptide was used with a tritium pressure of 700°–750° mm Hg°. The solution was magnetically stirred at 21° C. for 2.5–3.0 h. After removal of the excess tritium by evacuation, 50 mg of DTT in 0.5 ml of DMA was added. The solvent was then evaporated overnight at 21° C. to yield a brown-black residue. The residue was dissolved in 1–2 ml of a solution consisting of 5% HOAc AND 3% ethanol and submitted to a Sephadex G-10 column (20×400 mm) for desalting. Immediately after lyophilization of the peptide peak, it was chromatographed in a CMC column (10×500 mm) as previously described (Li et al., 1976), except that all buffers contained 3% ethanol (Evans, 1976). The contents in the major peak were lyophilized and submitted to partition chromatography on Sephadex G-50 in a 1.0×34 cm column in a solvent system consisting of butanol/pyridine/HOAc/$H_2O$ (5/0.04/1/4, v/v). The main component with $R_f$ of 0.31 was lyophilized and rechromatographed on CMC as above to give a symmetrical peak which contains the tritiated $\beta_h$-endorphin. The content in the peak tubes could be stored indefinitely at 4° C. The yield of triated $\beta_h$-endorphin was 1.4 mg with 50 Ci/mmole.

The amino analyses of acid hydrolysates of native and tritiated $\beta_h$-endorphin showed that their compositions were identical and completely in accordance with that expected. Paper electrophoresis at pH 6.7, followed by autoradiography, showed a single spot for native $\beta_h$-endorphin (ninhydrin) and for the tritiated peptide (radioactivity) with identical mobility. Paper chromatography in the solvent system, n-BuOH/HOAc/$H_2O$ (4/1/5, v/v) which readily separates native and iodinated $\beta_h$-endorphin, showed no trace of iodinated peptide. The tryptic map of tritiated $\beta_h$-endorphin gave rise to three radioactive spots corresponding to peptide fragments of Asn-Ala-Tyr-Lys, AspAla-Tyr-Lys, and Asx-Ala-Tyr-Lys-Lys, respectively.

The biological activity of tritiated $\beta_h$-endorphin was identical to the native peptide as assayed in preparations of guinea pig ileum [Kosterlitz, Brit. J. Pharm. 39, 398 (1970)] with $IC_{50}$ of $0.70 \times 10^{-8}$ M.

EXAMPLE 2

In analogy to the procedure of Example 1, [3,5-$I_2$-Tyr$^{27}$] $\beta_c$-endorphin, synthesized in accordance to the procedure of Example 3 of U.S. Pat. No. 4,038,222 using $N^\alpha$-Boc-3,5-$I_2$-Tyr(OBrBzl) in position 27 is tritiated to produce tritiated $\beta_c$-endorphin.

EXAMPLE 3

In analogy to Example 1, [3,5-$I_2$-Tyr$^{27}$]-$\beta_p$-endorphin, synthesized in accordance to the procedure of Example 5 of U.S. Pat. No. 4,038,222 utilizing $N^\alpha$-Boc-3,5-$I_2$-Tyr(OBrBzl) in position 27 of $\beta_p$-endorphin is tritiated to yield tritiated $\beta_p$-endorphin.

EXAMPLE 4

In analogy to Example 1, [3,5-$I_2$-Tyr$^1$]-$\beta_h$-endorphin synthesized using $N^\alpha$-Boc-3,5-$I_2$-Tyr(OBrBzl) to replace tyrosine in position 1 of $\beta_h$-endorphin is tritiated to yield tritiated $\beta_h$-endorphin.

EXAMPLE 5

In analogy to Example 1, [3,5-$I_2$-Tyr$^{1,27}$]-$\beta_h$-endorphin, synthesized using $N^\alpha$-Boc-3,5-$I_2$-Tyr(OBrBzl) to replace tyrosine in positions 1 and 27 of $\beta_h$-endorphin is tritiated to yield tritiated $\beta_h$-endorphin.

I claim:
1. Tritiated β-endorphin.
2. The tritiated compound of claim 1 which is β-human endorphin.
3. The tritiated compound of claim 1 which is β-porcine endorphin.
4. The tritiated compound of claim 1 which is β-camel endorphin.

* * * * *

UNITED STATES PATENT AND TRADEMARK OFFICE
CERTIFICATE OF CORRECTION

PATENT NO. : 4,219,468
DATED : August 26, 1980
INVENTOR(S) : Choh H. Li

It is certified that error appears in the above-identified patent and that said Letters Patent are hereby corrected as shown below:

On Title page, second line of Notice should read "subsequent to Jun. 20, 1995" instead of "subsequent to Jun. 20, 1992".

Signed and Sealed this

Thirtieth Day of December 1980

[SEAL]

Attest:

SIDNEY A. DIAMOND

Attesting Officer

Commissioner of Patents and Trademarks